United States Patent [19]
Pokorney et al.

[11] Patent Number: 5,104,387
[45] Date of Patent: Apr. 14, 1992

[54] BI-PLANAR FLUID CONTROL VALVE

[75] Inventors: James L. Pokorney; William R. Kramlinger, both of Shoreview, Minn.

[73] Assignee: St. Jude Medical, Inc., St. Paul, Minn.

[21] Appl. No.: 528,485

[22] Filed: May 25, 1990

[51] Int. Cl.$^5$ .............................................. A61M 5/05
[52] U.S. Cl. ................................. 604/248; 137/625.47
[58] Field of Search ............................. 604/246, 248; 137/625.47

[56] References Cited

U.S. PATENT DOCUMENTS

| | | | |
|---|---|---|---|
| D. 271,421 | 11/1983 | Fetterman . | |
| 2,921,604 | 1/1960 | Zettl | 137/625.47 |
| 3,048,192 | 8/1962 | Murphy . | |
| 3,139,907 | 7/1964 | Jones | 137/625.47 |
| 3,157,201 | 11/1964 | Littmann . | |
| 3,834,372 | 9/1974 | Turney | 604/248 X |
| 3,957,082 | 5/1976 | Fuson et al. | 604/248 X |
| 4,193,406 | 3/1980 | Jinotti . | |
| 4,287,907 | 9/1981 | Worthy | 137/255 |
| 4,300,572 | 11/1981 | Knighton . | |
| 4,446,867 | 5/1984 | Leveen et al. . | |
| 4,566,480 | 1/1986 | Parham . | |
| 4,589,280 | 5/1986 | Carter . | |
| 4,604,093 | 8/1986 | Brown et al. . | |
| 4,648,868 | 3/1987 | Hardwick et al. | 604/248 X |
| 4,687,475 | 8/1987 | Tai et al. . | |
| 4,758,235 | 7/1988 | Tu | 604/248 |
| 4,789,000 | 12/1988 | Aslanian | 604/248 X |
| 4,790,193 | 12/1988 | Moriuchi et al. | 73/756 |
| 4,819,694 | 4/1989 | Jiang | 137/625.47 |
| 4,950,230 | 8/1990 | Kendell | 604/248 X |
| 4,967,797 | 11/1990 | Manska | 604/248 X |

Primary Examiner—C. Fred Rosenbaum
Assistant Examiner—Corrine Maglione
Attorney, Agent, or Firm—Leydig, Voit & Mayer

[57] ABSTRACT

A fluid control valve has a valve body with a cylindrical bore and a plurality of channels which communicate between the bore and the outside of the valve body. The inner ends of at least two of the channels lie in a first plane, and the inner end of at least one of the channels lie in a second plane. A valve stem rotatably mounted in the bore has two independent channels. One of the channels has two ends lying in the first plane, while the other channel has one end lying in the first plane and the other end lying in the second plane.

14 Claims, 15 Drawing Sheets

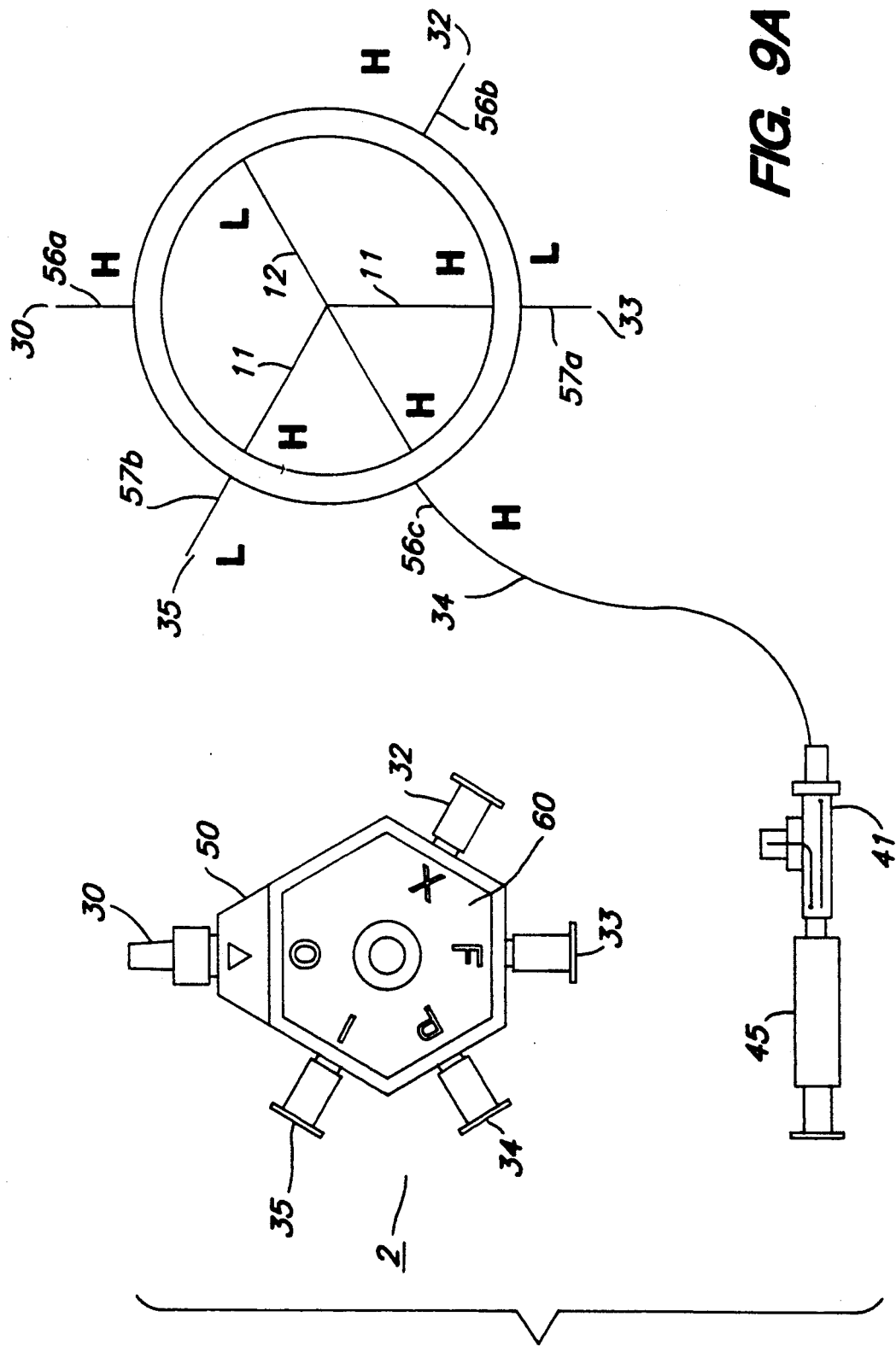

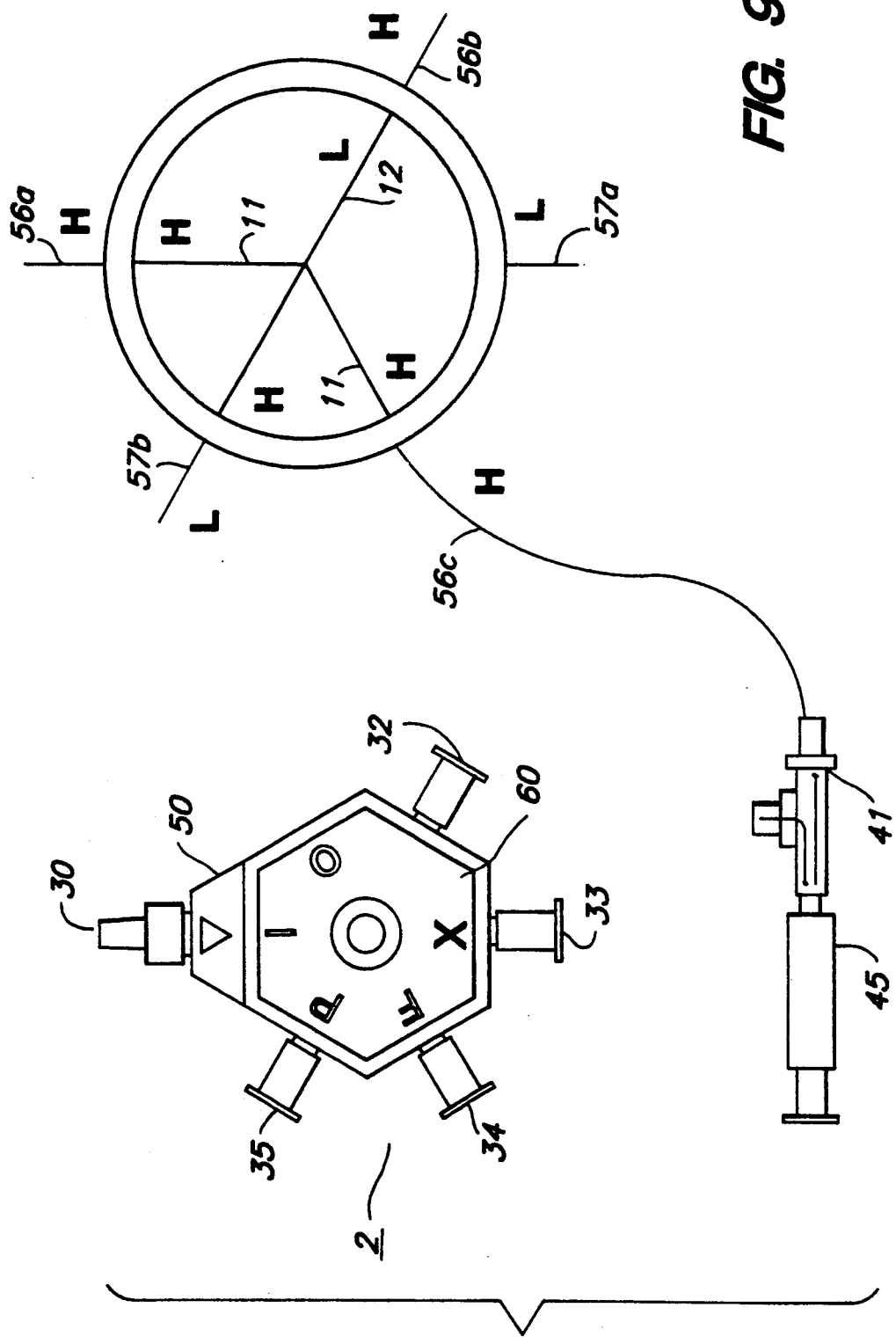

BI-PLANAR FLUID CONTROL VALVE

BACKGROUND OF THE INVENTION

This invention relates to a fluid control valve. More particularly but not exclusively, the invention relates to a fluid control valve suitable for use in medical procedures such as arteriography and angioplasty.

Various medical procedures involve the introduction of fluids into the body of a patient using a catheter. When a series of different fluids are to be administered, it is necessary to completely flush one fluid from the catheter before the next fluid is administered. For example, during arteriography or angioplasty, the lines must be flushed with saline before and after the addition of contrast media. When this is done, it is important that no contaminant be permitted to pass to the patient along with the fluid, since the presence of contaminant creates the risk of injury, infection or an embolism, with possibly fatal consequences. Furthermore, before the fluids can be introduced, it may be necessary to purge the injection line of air. After the air has been purged it is important to prevent the reintroduction of air. Therefore, it is necessary to be able to selectively connect the catheter to any one of a number of devices, such as fluid reservoirs for contrast dye or saline solution, exhaust ports, and pressure ganges without allowing air or contaminants to enter the catheter. The most commonly used apparatus for connecting a catheter with other equipment is a manifold which consists of a plurality of three-way stopcocks connected in series. One of the stopcocks is connected to the catheter, while the other stopcocks are connected to other pieces of equipment. By selectively opening and closing the stopcocks, the catheter can be made to communicate with any one of the pieces of equipment.

A conventional stopcock manifold has a number of problems which make it not only difficult but potentially dangerous to use. Since a plurality of stopcocks must be manipulated to achieve a desired flow path to the catheter, it takes a considerable degree of training to learn how to properly set all the stopcocks. Furthermore, as it is not immediately evident from looking at the manifold which way fluid is flowing, it is quite easy to make an improper connection. This could result in a fluid being mistakenly passed into a patient's body via the catheter, or in a high-pressure fluid being mistakenly applied to a pressure transducer having a low rated pressure, causing damage to the transducer.

Furthermore, a stopcock manifold includes a large number of moving parts, so it is expensive to manufacture. In addition, since the manifold usually has at least three stopcocks, there is a tendency to make each stopcock as small as possible in order to minimize the size of the manifold. The resulting stopcocks have very small handles which are difficult to grasp and manipulate.

SUMMARY OF THE INVENTION

Accordingly, it is an object of the present invention to provide a fluid control valve which can be operated using only a single handle.

It is another object of the present invention to provide a fluid control valve which has a simple structure and is inexpensive to manufacture.

It is another object of the present invention to provide a fluid control valve which enables a user to quickly and safely switch between functions, particularly while performing a medical procedure on a patient.

It is another object of the present invention to provide a fluid control valve which has a smaller filling volume than a conventional stopcock manifold.

It is yet another object of the present invention to provide a fluid control valve which indicates to a user the function which is being performed by the valve.

A fluid control valve according to the present invention includes a valve body having a cylindrical bore and at least three channels formed therein. Each of the channels has an inner end which opens onto the bore and an outer end which communicates with the outside of the valve body. The inner end of at least two of the channels lie in a first plane and the inner end of at least one of the channels lies in a second plane which differs from the first plane. A valve stem which is rotatably mounted in the bore of the valve body has two independent channels for connecting predetermined channels in the valve body with one another. One of the channels in the stem has ends in the first plane, while the other channel has a first end in the first plane and a second end in the second plane.

The number of channels in the valve body is not critical. When the valve is to be used for administration of a fluid to a patient via a catheter, it is usually desirable to have at least four channels, including one for the catheter, a second channel for a syringe, a third channel for a saline solution for flushing the catheter, and a fourth channel for an exhaust port. Additional channels may be provided for other equipment, such as a channel for a pressure transducer to measure the pressure in the catheter or a channel for an additional exhaust port.

A fluid control valve according to the present invention is particularly suited for the administration of fluids used in medical procedures such as angiography and angioplasty but it can be used to control the flow of any fluid, wherein the term "fluid" is intended to encompass both liquids and gases.

BRIEF DESCRIPTION OF THE DRAWINGS

FIGS. 9A through 9E are schematic illustrations of the handle orientation and the fluid flow paths for various settings of the embodiment of FIG. 6.

DESCRIPTION OF THE PREFERRED EMBODIMENTS

Figure 1:
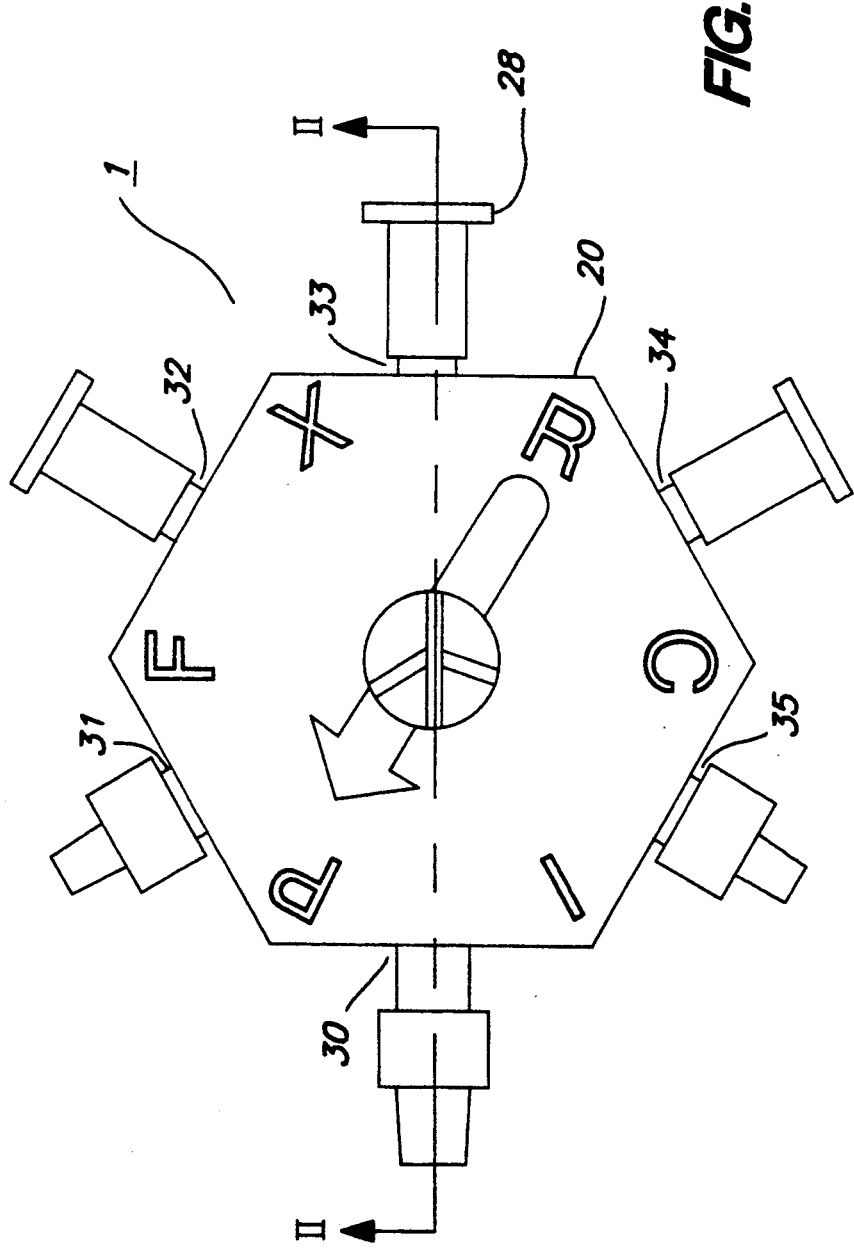
FIG. 1 is a plan view of a first embodiment of a fluid control valve according to the present invention.
Figure 2:
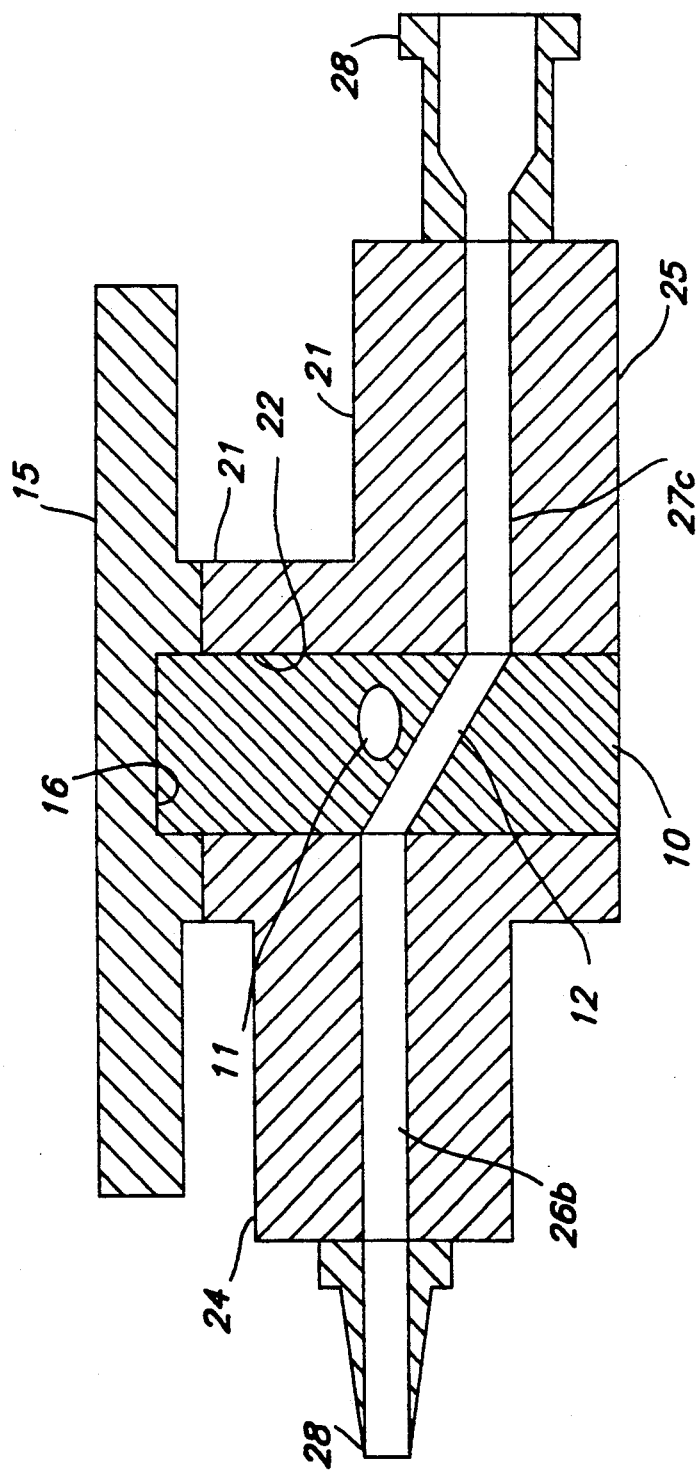
FIG. 2 is a vertical cross-sectional view taken along Line II—II of FIG. 1.

A number of preferred embodiments of a fluid control valve according to the present invention will now be described while referring to the accompanying drawings. FIGS. 1 and 2 are respectively a plan view and a cross-sectional view of a first embodiment. As shown in these figures, a valve 1 according to the present invention includes a valve body 20 having a cylindrical bore in which a valve stem 10 is rotatably mounted. The valve stem 10 can be rotated to a plurality of positions by a handle 15 which is secured to one end of the stem 10. Six channels for fluid flow are formed in the valve body 20, and specific channels can be connected with one another through the valve stem 10 by rotation of the valve stem 10 to predetermined positions.

Figure 3A:
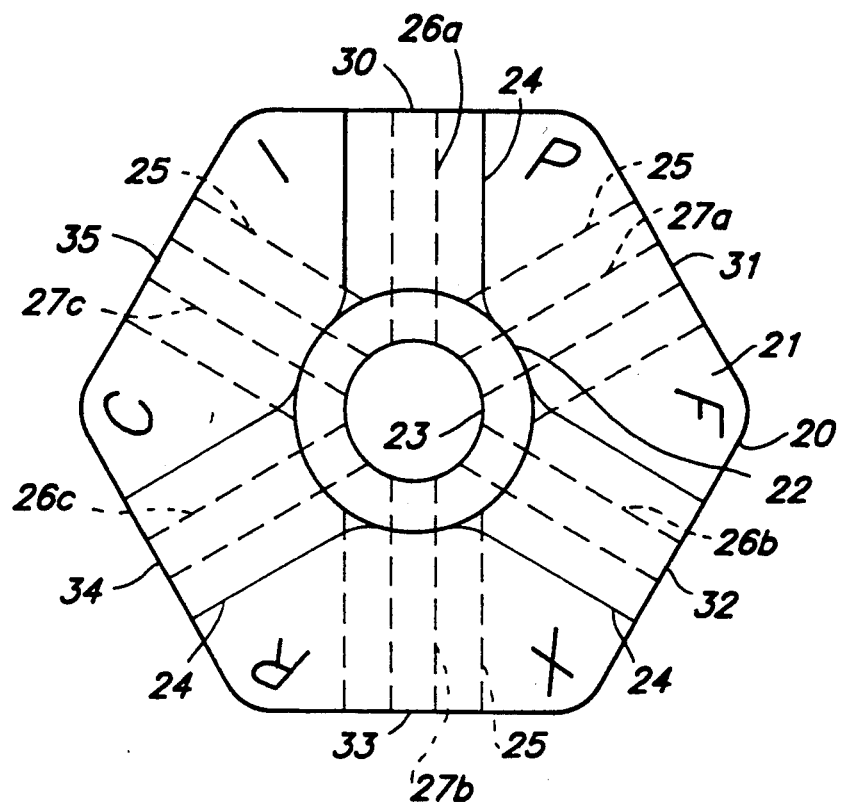
FIGS. 3A and 3B are respectively a plan view and a side view of the valve body of the embodiment of FIG. 1.
Figure 3B:
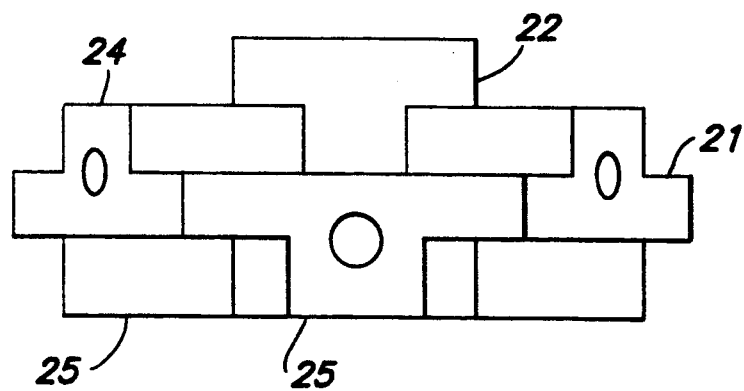

The shape of the valve body 20 is not critical, but in this embodiment, the valve body 20 has the shape of a regular hexagon when viewed in plan. As shown in FIGS. 3A and 3B, the valve body 20 has a hexagonal base 21 with a cylindrical boss 22 at its center which extends from the top and bottom surfaces of the base 21. A cylindrical bore 23 for journaling the valve stem 10 is formed at the center of the boss 22. Three upper ribs 24 are formed on the top surface of the base 21 at intervals of 120°. Each rib 24 extends from the boss 22 to the outer periphery of the base 21. Three similar lower ribs 25 are formed on the bottom surface of the base 21 at intervals of 120°. As viewed in plan, the upper ribs 24 are displaced by 60° with respect to the lower ribs 25. The upper and lower ribs can be integral with the base.

First through third upper channels 26a–26c are formed in the upper ribs 24, and first through third lower channels 27a–27c are formed in the lower ribs 25. Each channel extends radially through one of the ribs and has an inner end which opens onto the inside of the cylindrical bore 23 and an outer end which opens onto the outer peripheral surface of the valve body 20. The inner ends of the upper channels 26a–26c all lie in a first plane, while the inner ends of the lower channels 27a–27c all lie in a second plane which is parallel to and spaced from the first plane. In this embodiment, the channels are all straight and lie in the same planes as the inner ends thereof. However, as long as the inner ends of a plurality of the channels lie in the first plane and the inner ends of the remaining channels lie in the second plane, there are no restrictions on the shapes of the channels or the locations of their outer ends.

The outer ends of the channels serve as fluid ports through which fluids can enter or leave the valve 1. In this embodiment, the valve 1 includes six ports, which will be referred to as a catheter port 30, a contrast dye port 31, a saline flush port 32, a transducer port 33, a syringe port 34, and a flush exhaust port 35. The catheter port 30, the saline flush port 32, and the syringe port 34 communicate with the upper channels 26a–26c, respectively, while the contrast dye port 31, the transducer port 33, and the flush exhaust port 35 communicate with the lower channels 27a–27c, respectively. In a preferred embodiment, the filling volume ranges from about 0.02 in$^3$ to about 0.03 in$^3$.

The valve body 20 can be made of any material which is compatible with the fluid being handled and which can be sanitized when the valve is to be used for medical applications. A transparent molded plastic is particularly suitable for the valve body 20 because it enables a user to easily ascertain the presence of air bubbles in the channels.

The outer ends of the channels can be equipped with conventional male or female Luer connectors 28 for connecting the channels to external equipment, although any other type of suitable connector can instead be used. The outer ends of the channels can be threaded if necessary to enable the Luer connectors 28 to be mounted on the valve body 20. In the preferred embodiment, the Luer connector may be molded integrally to the valve body.

The valve body 20 need not have the structure illustrated in FIGS. 3A and 3B. For example, it could be in the form of a simple hexagonal block having a bore and channels formed therein and without any boss or ribs. However, the ribs 24 and 25 make the valve body 20 easier to grasp and result in a structure which is adequately rigid yet lighter than a solid block. Furthermore, the valve body 20 need not be hexagonal, and many other shapes are possible.

Figure 4A:
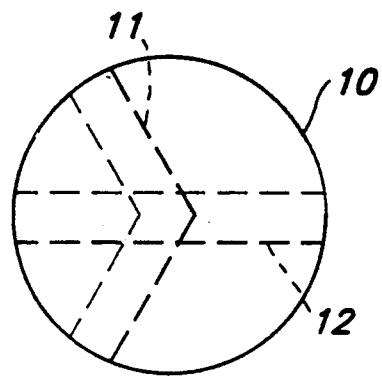
FIGS. 4A and 4B are respectively a plan view and an elevation of the valve stem of the embodiment of FIG. 1.
Figure 4B:
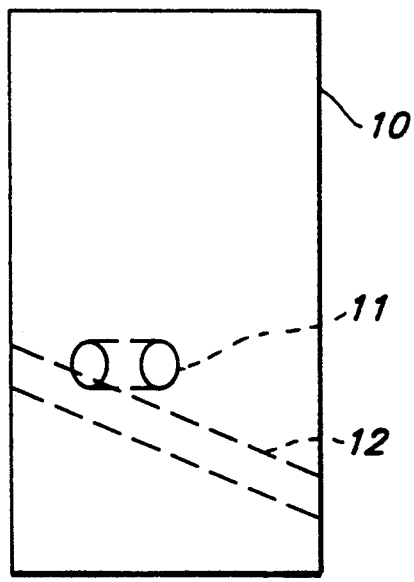

As shown in FIGS. 4A and 4B, the valve stem 10 is a rod-shaped member having two channels 11 and 12 formed therein. The first channel 11, which will be referred to as the 120° channel, has two branches that extend radially outwards from the longitudinal center of the stem 10 at angles of 120° with respect to one another. The radially outer ends of the branches of the 120° channel 11 open onto the outer surface of the stem 10 at the same height as one another as shown in FIG. 4B. The second channel 12, which extends diagonally through the stem 10, is straight and will be referred to as the straight channel. It has an upper end which opens onto the outer surface of the stem 10 at the same level as the openings of the 120° channel 11 and a lower end which opens onto the outside of the stem 10 at a different level (for convenience, a lower level is illustrated). When the stem 10 is viewed in plan, as in FIG. 4A, the straight channel 12 bisects the angle formed by the two branches of the 120° channel 11. The upper end of the straight channel 12 is the end which is closest to the ends of the 120° channel 11 as viewed in plan. When the valve stem 10 is inserted into the valve body 20, the ends of the 120° channel 11 and the upper end of the straight channel 12 lie in the first plane, i.e., the plane containing the inner ends of the upper channels 26a–26c in the upper ribs 24 of the valve body 20, while the lower end of the straight channel 12 lies in the second plane containing the inner ends of the lower channels 27a–27c in the lower ribs 25.

The handle 15 has a central cavity 16 which fits over the top of the valve stem 10 as shown in FIG. 2. The handle 15 can be secured to the valve stem 10 by any suitable means, such as by press-fitting, with an adhesive, ultrasonic welding, by a set screw or may be molded integrally with the valve stem. The stem 10 may be equipped with a mechanism for ensuring that the handle 15 and the valve stem 10 are properly aligned with respect to one another. For example, the stem 10 can be equipped with a key which fits into a corresponding keyway in the handle 15 when the stem 10 and the handle 15 are properly aligned. Like the valve body 20, the valve handle 15 may be made of a transparent molded plastic to enable a user to easily spot air bubbles in the flow channels of the valve 1. One end of the handle 15 may be in the shape of an arrow 17 (FIG. 1). While rotating the handle 15, detent stops can be created at each port alignment through the use of intermittent interference fits between the valve body 20 and either the valve stem 10 or handle 15. These stops make it easy for a user to determine when port alignment has been reached.

For ease of use, the valve stem 10 preferably includes a setting indicator which indicates to a user the setting of the valve at any given time. In an embodiment of the invention, the indicator comprises symbols formed on the top surface of the base of the valve body 20. The particular symbols which are utilized are not critical, as long as different symbols are employed for different valve positions. Thus, the operator of the device can quickly and accurately align the ports by turning the valve handle to point to the appropriate symbols and aligning the colored passageways in the handle with the appropriate colored ports on the valve body. For example, when the valve is to be used for angioplasty or arteriography, the symbols can be letters which indicate the function which is being performed at a particular valve setting. In the illustrated embodiment, the symbols P, F, X, R, C, and I are employed. P stands for pressure, F stands for flush, X stands for exhaust, R stands for rinse, C stands for contrast, and I stands for inject. When the arrow 17 on the handle 15 points to one of the symbols, the valve setting is such that the function indicated by the symbol can be performed. The symbols can be formed on the valve body 20 by any suitable method, such as by printing or engraving. If the valve body 20 is a molded plastic, the symbols can be formed during molding.

The handle 15 of an embodiment of the invention may also include a flow indicator 18 which indicates to a user the flow path of fluid at any setting of the valve 1. The flow indicator 18 comprises two lines forming a 120° angle and a third line which bisects the 120° angle. The intersection of the lines coincides with the longitudinal axis of the valve stem 10. With the handle 15 properly mounted on the stem 10, as viewed in plan, the lines of the flow indicator 18 forming the 120° angle coincide with the centerline of the 120° channel 11 of the valve stem 10, while the straight line of the flow indicator 18 coincides with the centerline of the straight channel 12. For example, FIG. 1 illustrates the flush function; the setting indicator is pointing to "F" and the flow indicator shows that the channel for flush port 32 are aligned with the channel for the catheter port 30.

In order to make it easier for a user to identify the flow path of fluid through the valve 1, the symbols on the valve body 20 and the flow indicator 18 may be color-coded. For example, the letters F, R, and I and the 120° line on the handle 15 can be a first color, while the letters X, C, and P and the straight line on the handle 15 can be a second color. When the arrow 17 on the handle 15 points to a letter of the first color, the user will know that fluid is flowing through the valve 1 along the path shown by the lines of the same color on the handle 15.

Figure 5:
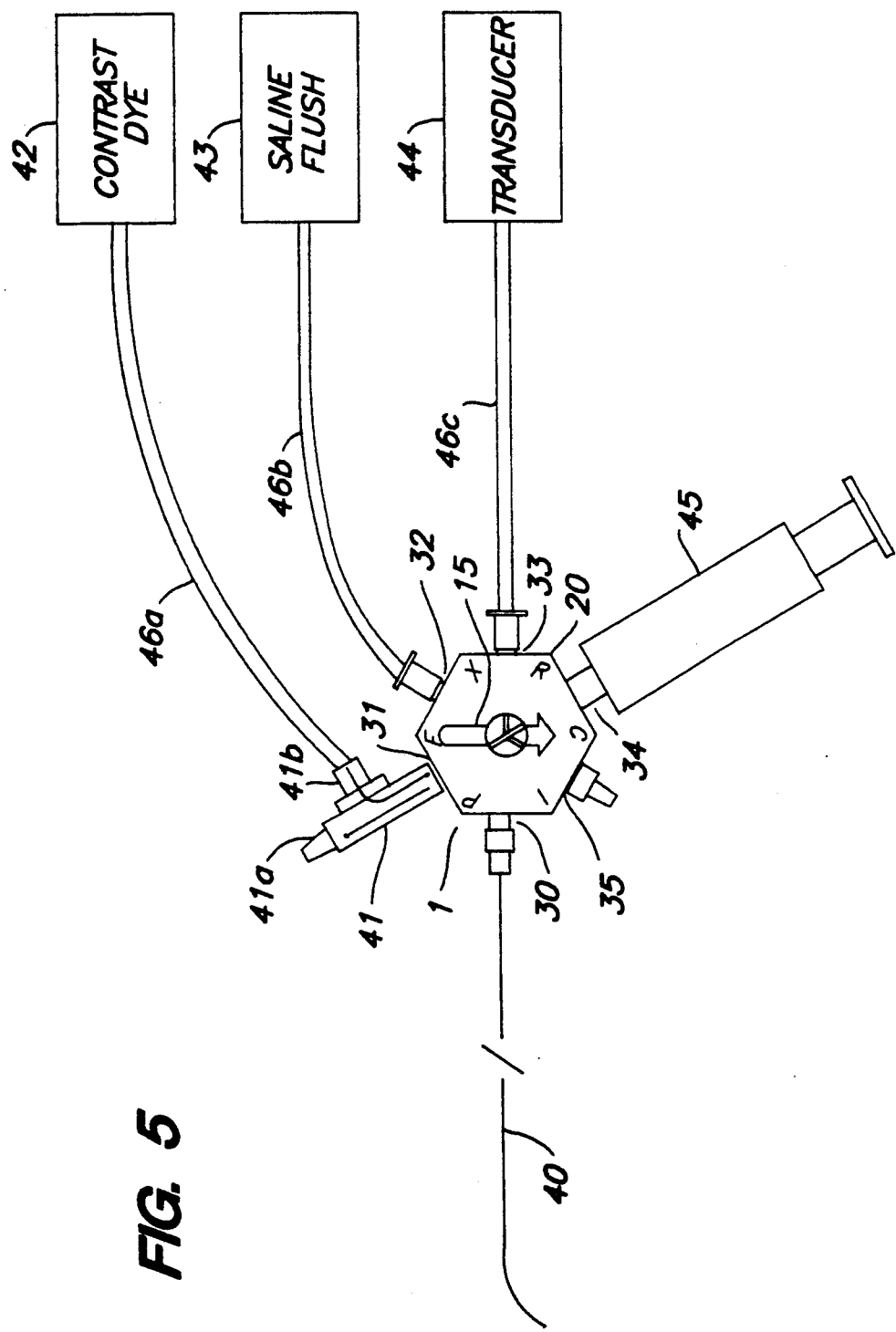
FIG. 5 is a schematic plan view of an example of an arrangement for administration of a fluid using the embodiment of FIG. 1.

FIG. 5 schematically illustrates a typical arrangement employing the valve 1 of FIG. 1 for administering a contrast die to a patient using a catheter. Moving clockwise round the valve 1 in FIG. 5, a catheter 40 is connected to the catheter port 30. A conventional dual check valve 41, such as a Burron Medical #S-5401122 dual check valve, is connected to the contrast dye port 31. The dual check valve 41 has a syringe exhaust port 41a, which can be connected to a reservoir for waste fluids, and an inlet 41b, which is connected by tubing 46a to a reservoir 42 for a contrast dye. As shown by the arrows in FIG. 5, the check valve 41 allows one-way flow from the inside of the valve body 20 through the syringe exhaust 41a or from the contrast dye reservoir 42 into the valve body 20. The saline flush port 32 is connected to a reservoir 43 for a saline solution by tubing 46b. The transducer port 33 is connected to a pressure transducer 44 by tubing 46c. The syringe port 34 is connected to a syringe 45. The flush exhaust port 35 can be connected to an unillustrated container for waste fluids. The catheter 40, the dual check valve 41, the contrast dye reservoir 42, the saline flush reservoir 43, the pressure transducer 44, and the syringe 45 are all standard components for use in medical procedures.

When the handle 15 is turned to the P (pressure) position, the straight channel 12 in the valve stem 10 connects the catheter port 30 with the transducer port 33. In this position, the pressure transducer 44 can measure the pressure in the catheter 40. As viewed in plan, the branches of the 120° channel 11 in the valve stem 10 are aligned with the first lower channel 27a (leading to the contrast dye port 31) and the third lower channel 27c (leading to the flush exhaust port 35). However, as the ends of the 120° channel 11 lie in the first plane and the ends of the lower channels 27a and 27c lie in the second plane, there is no flow through the 120° channel 11.

When the handle 15 is turned to the F (flush) position, the 120° channel 11 in the valve stem 10 connects the catheter port 30 with the saline flush port 32. In this position, the catheter 40 can be flushed with saline solution from the saline flush reservoir 43. At this time, the straight channel 12 of the valve stem 10 is not connected to any of the channels in the valve body 20, so there is no flow through the straight channel 12.

When the handle 15 is turned to the X (exhaust) position, the straight channel 12 connects the saline flush port 32 with the flush exhaust port 35. In this position, the saline solution can be passed through the straight channel 12 to remove any other fluid or air bubbles from the straight channel 12. At this time, the 120° is not active.

If the handle 15 is turned to the R (rinse) position, the 120° channel 11 connects the saline flush port 32 with the syringe port 34. In this position, if the plunger of the syringe 45 is retracted, saline solution can be drawn into the syringe 45. There is no flow through the straight channel 12.

When the handle 15 is in the C (contrast/exhaust) position, the straight channel 12 of the valve stem 10 connects the syringe port 34 with the contrast dye port 31. If the plunger of the syringe 45 is retracted, contrast dye can be drawn from the contrast dye reservoir 42 and into the syringe 45. In the same setting, if the plunger of the syringe 45 is depressed, fluid and air bubbles can be discharged from the syringe 45 and exhausted from the system through the syringe exhaust port 41a of the check valve 41.

When the handle 15 is turned to the I (inject) position, the 120° channel 11 connects the catheter port 30 with the syringe port 34. In this position, if the plunger of the syringe 45 is depressed, fluid (such as contrast dye) can be transferred from the syringe 45 into the catheter 40.

If the plunger of the syringe 45 is retracted, fluid or air bubbles can be withdrawn from the catheter 40.

The above-described valve positions are summarized in the following table.

TABLE 1

| Handle Position | Color Code * | Active Channel in Valve Stem | Clinical Function |
| --- | --- | --- | --- |
| P (pressure) | B | straight | Monitor fluid pressure in catheter. |
| F (flush) | A | 120° | Flush saline through catheter. |
| X (exhaust) | B | straight | Exhaust fluid or air bubble from flush exhaust port. |
| R (rinse) | A | 120° | Fill syringe with fluid from saline reservoir. |
| C (contrast/exhaust) | B | straight | Load contrast dye into the syringe; exhaust fluid or air bubbles from syringe. |
| I (inject) | A | 120° | Inject contrast dye or saline into catheter; aspirate fluid or air bubbles from catheter. |

*A and B designate two different colors.

Figure 6:
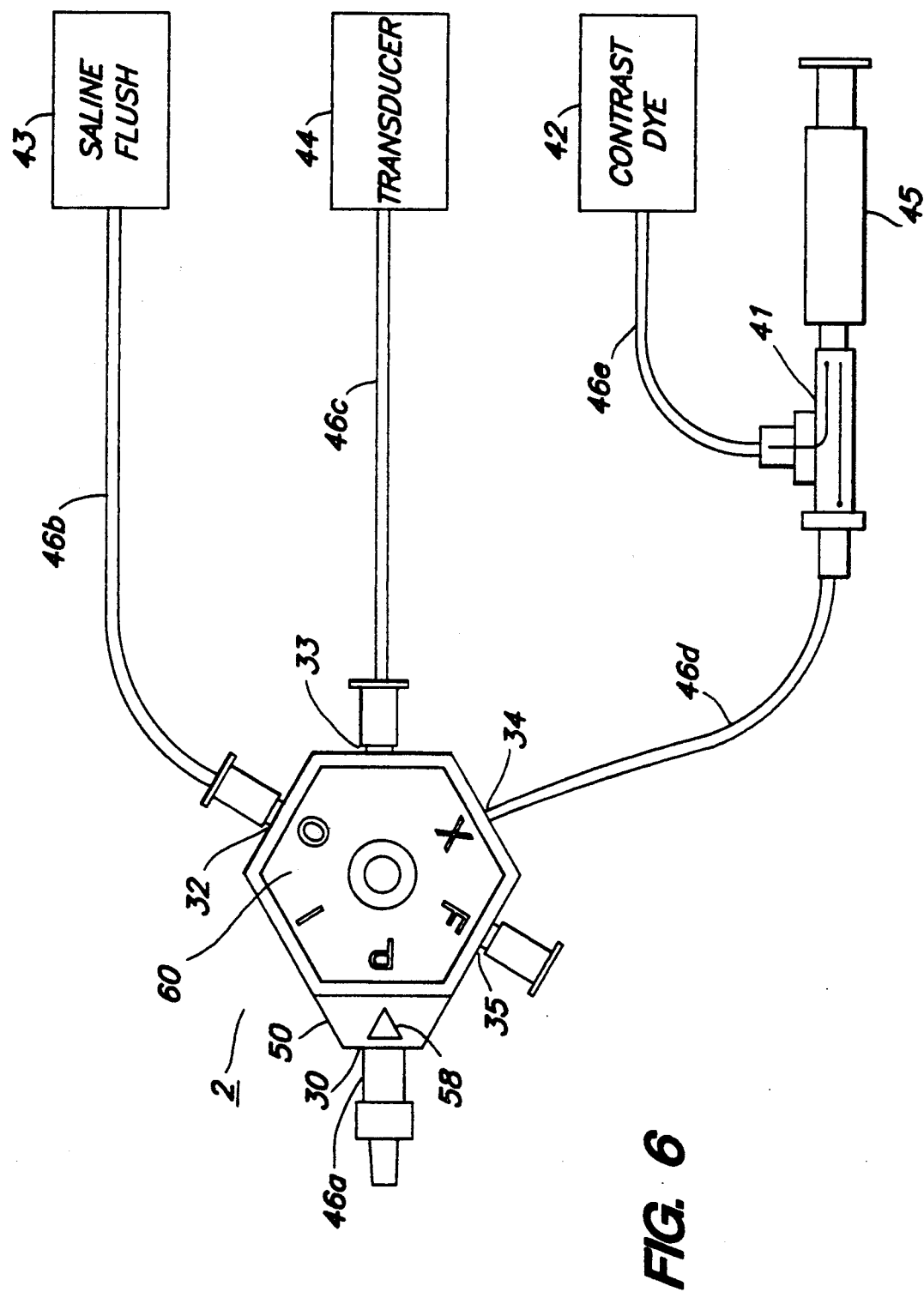
FIG. 6 is a schematic plan view of an example of an arrangement for administration of a fluid using a second embodiment of the present invention.

The embodiment of FIG. 1 is equipped with 6 fluid ports. However, the number of ports is not critical. FIG. 6 schematically illustrates another embodiment of a control valve 2 which is equipped with five fluid ports. Like the embodiment of FIG. 1, it includes a catheter port 30, a saline flush port 32, a transducer port 33, a syringe port 34, and a flush exhaust port 35. In this embodiment, however, the contrast dye port 31 of FIG. 1 has been deleted, and a contrast dye reservoir 42 is connected to the syringe port 34 via a dual check valve 41.

Figure 7A:
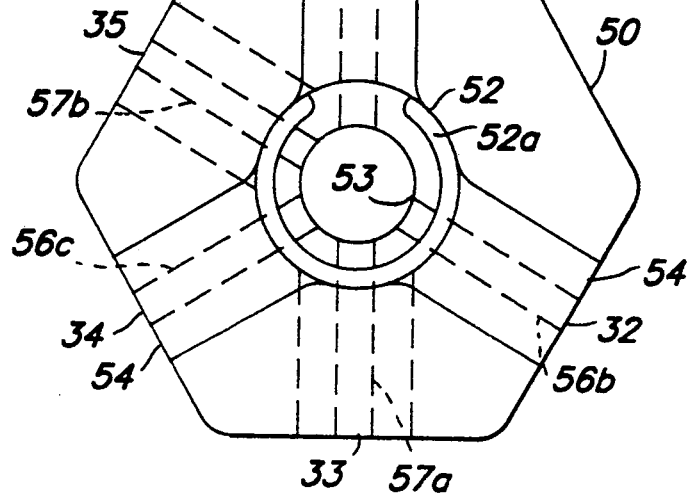
FIGS. 7A through 7C are respectively a top view, a side view, and bottom view of the valve body of the embodiment of FIG. 6.
Figure 7B:
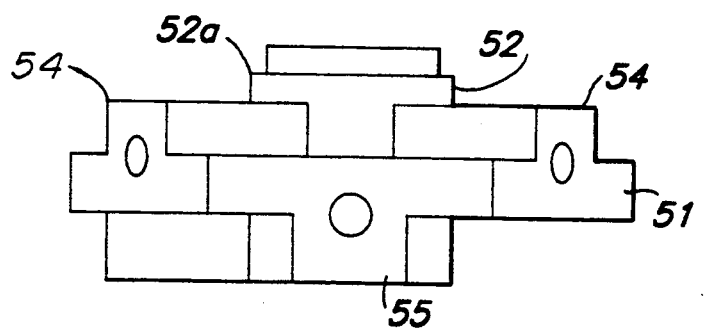
Figure 7C:
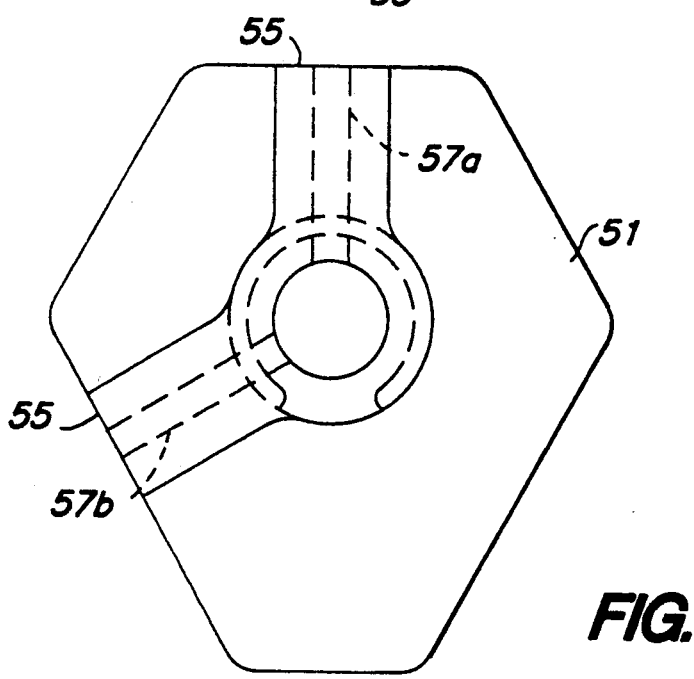

FIGS. 7A-7C are respectively a top view, a side view, and a bottom view of the valve body 50 of the embodiment illustrated in FIG. 6. It is similar in structure to the valve body 20 of FIG. 3A, but instead of having the profile of a regular hexagon, the two sides of the upper half of the valve body 50 in FIG. 7A are longer than the corresponding sides of the lower half of the valve body 50. Three upper ribs 54 spaced apart from one another by 120° are formed on the top surface of the base 51 of the valve body 50, while two lower ribs 55 spaced apart from one another by 120° are formed on the bottom surface. A boss 52 having a cylindrical bore 53 is formed on the base 51 where the centerlines of the ribs intersect one another. First through third upper channels 56a-56c are formed in the upper ribs 54 between the inner surface of the bore 53 and the outer periphery of the valve body 50. Similarly, first and second lower channels 57a and 57b are formed in the two lower ribs 55. A ledge 52a is formed on the upper end of the boss 52. The ledge 52a extends circumferentially almost all the way around the boss 52 except for a sector which defines abutments for stopping the rotation of the handle 60 of the valve 2.

Figure 8A:
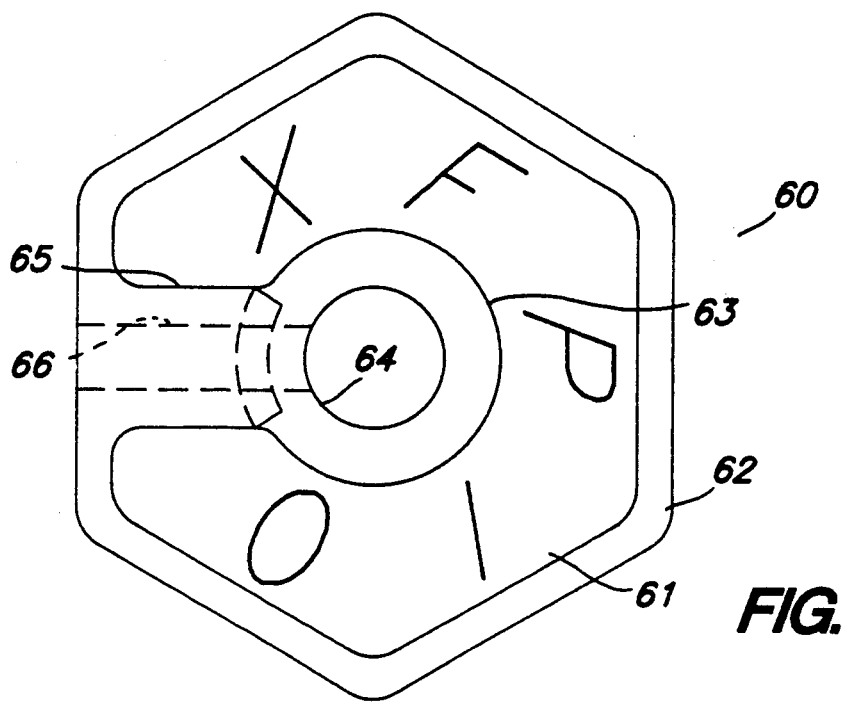
FIGS. 8A through 8C are respectively a top view, a transverse cross section, and a bottom view of the handle of the embodiment of FIG. 6.
Figure 8B:
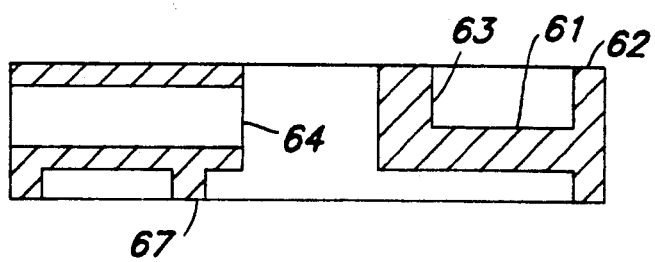
Figure 8C:
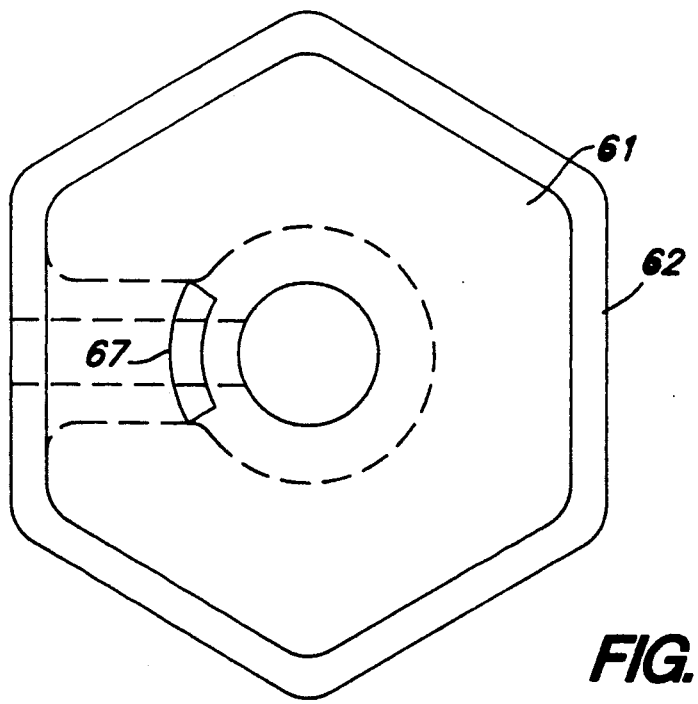

FIGS. 8A-8C are respectively a top view, a transverse cross section, and a bottom view of the handle 60. In the illustrated embodiment, the handle is in the shape of a regular hexagon with six sides of equal length. Each side has the same length as the three lower sides of the valve body 50 in FIG. 7A. The handle includes a flat base 61 having a hexagonal rim 62 formed along its outer periphery. A boss 63 with a cylindrical bore 64 is formed at the center of the base 61 and is connected with the rim 62 by a radially-extending rib 65. The bore 64 fits over the upper end of a valve stem 10, such as that illustrated in FIG. 4B, and the valve stem 10 is rotatably disposed in the bore 53 of the valve body 50. A radially-extending hole 66 for a set screw is formed in the rib 65 between the outer periphery of the handle 60 and the inner periphery of the bore 64. A projection 67 extends perpendicularly from the lower surface of the base 61. The projection 67 sits on the ledge 52a of the boss 52 of the valve body 50 and limits the rotation of the handle 60 when the projection 67 contacts the end surfaces of the ledge 52a.

Letters or other symbols indicating the setting of the valve 2 can be formed on the top surface of the base 61 of the handle 60 by engraving, printing, or other suitable method (as shown in FIG. 6). This embodiment employs the symbols X, F, P, and I which are used in FIG. 1, and in addition the symbol O, which represents an off position in which there is no flow of fluid through the valve 2, i.e., no channels are aligned. The valve 2 is in one of five possible settings whenever one of the sides of the valve handle 60 is flush with one of the three lower sides of the valve body 50. As shown in FIG. 6, a marker 58 can be formed on the elongated upper portion of the valve body 50 to indicate the symbol corresponding to the function which can be performed at the present setting of the valve 2.

There are no restrictions on the material of which the valve handle 60 can be made. It is preferable, however, that valve body 50 be made of a transparent material, such as a clear molded plastic, to enable a user to observe air bubbles in the channels of the valve body 50.

FIG. 6 shows a typical arrangement of equipment when using this embodiment for a medical procedure such as arteriography. The catheter port 30 can be connected to a catheter 40 by tubing 46a having a rotatable male Luer connector 47 at its outer end. The saline flush port 32 is connected by tubing 46b to a reservoir 43 for saline solution. The transducer port 33 is connected by tubing 46c to a pressure transducer 44. The syringe port 34 is connected by tubing 46d to a dual check valve 41. The check valve 41 has two ports, one of which is connected by tubing 46e to a reservoir 42 for a contrast dye, while the other port is connected to a syringe 45. As shown by the arrows in the figure, the check valve 41 allows one-way flow from the contrast dye reservoir 42 to the syringe 45 or from the syringe 45 into the valve body 50. The flush exhaust port 35 can be connected to an unillustrated reservoir for waste fluids. In a preferred embodiment, the filling volume range is between about 0.02 in$^3$ and about 0.03 in$^3$.

FIGS. 9A-9E show the orientation of the handle 60 and the flow paths of fluids for each of the positions of the valve 2 of FIG. 6. In these figures, an H indicates an opening for fluid lying in the first plane (the inner end of one of the upper channels 56a-56c in the valve body 50, the ends of the 120° channel 11, or the upper end of the straight channel 12 in the valve stem 10), while an L indicates an opening for fluid lying in the second plane (the inner end of one of the lower channels 57a or 57b in the valve body 50 or the lower end of the straight channel 12 in the valve stem 10).

FIG. 9A shows the valve 2 in the O (off) position. In this position, neither of the channels 11 or 12 in the valve stem 10 is connected with a channel in the valve body 50, so there is no flow through the valve 2. This position can be used for changing fittings or injecting the contrast dye into the syringe 45 by retracting the plunger of the syringe 45.

In FIG. 9B, the valve 2 is shown in the I (inject) position. The 120° channel 11 of the valve stem 10 connects the syringe port 34 with the catheter port 30, so when the plunger of the syringe 45 is depressed, the contrast dye can be forced into the catheter 40 via the dual check valve 41.

Figure 9C:
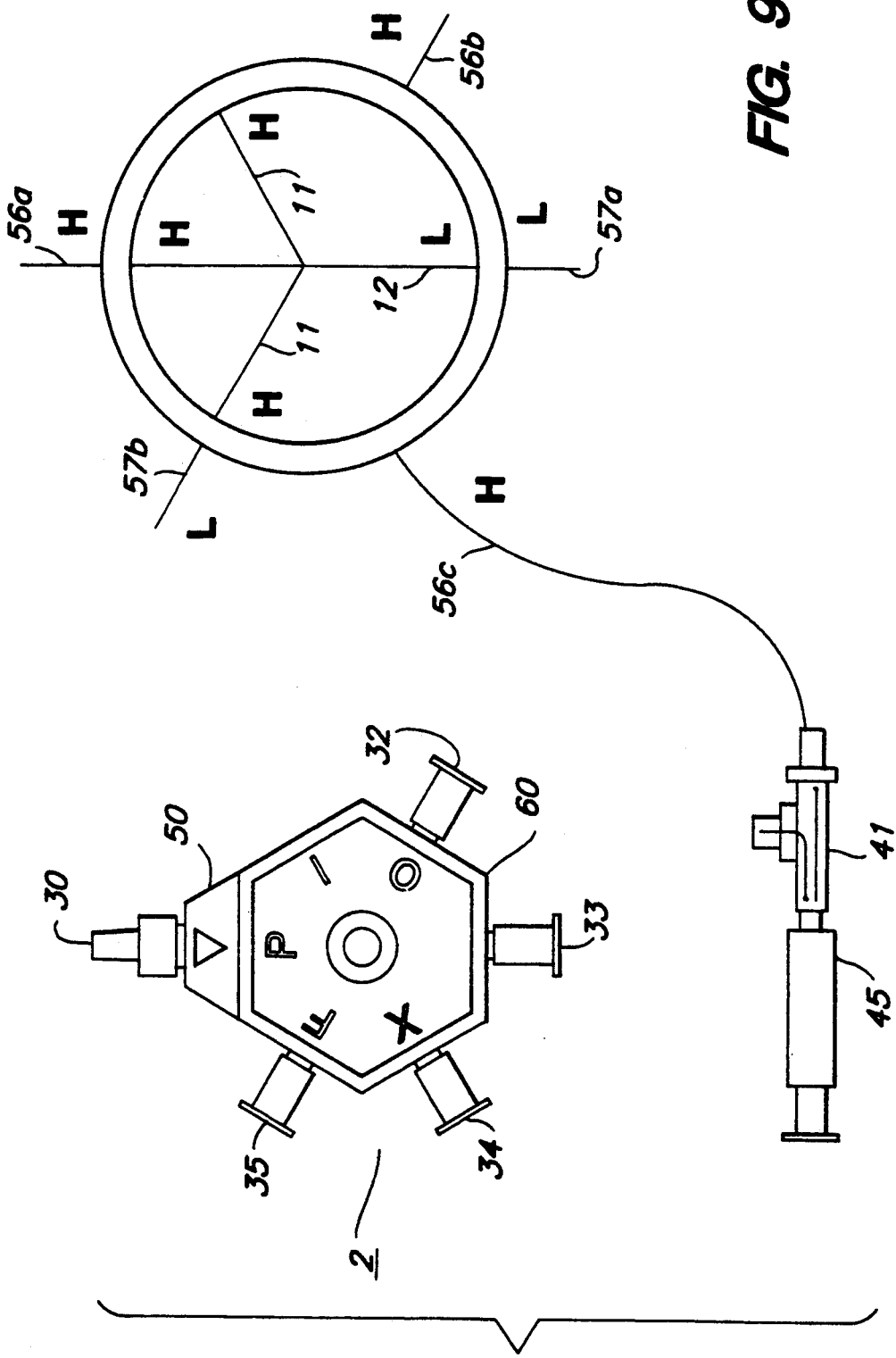

FIG. 9C illustrates the valve 2 in the P (pressure) position. The straight channel 12 of the valve stem 10 connects the transducer port 33 with the catheter port 30, so the pressure inside the catheter 40 can be measured. At the same time, the contrast dye can be loaded into the syringe 45.

Figure 9D:
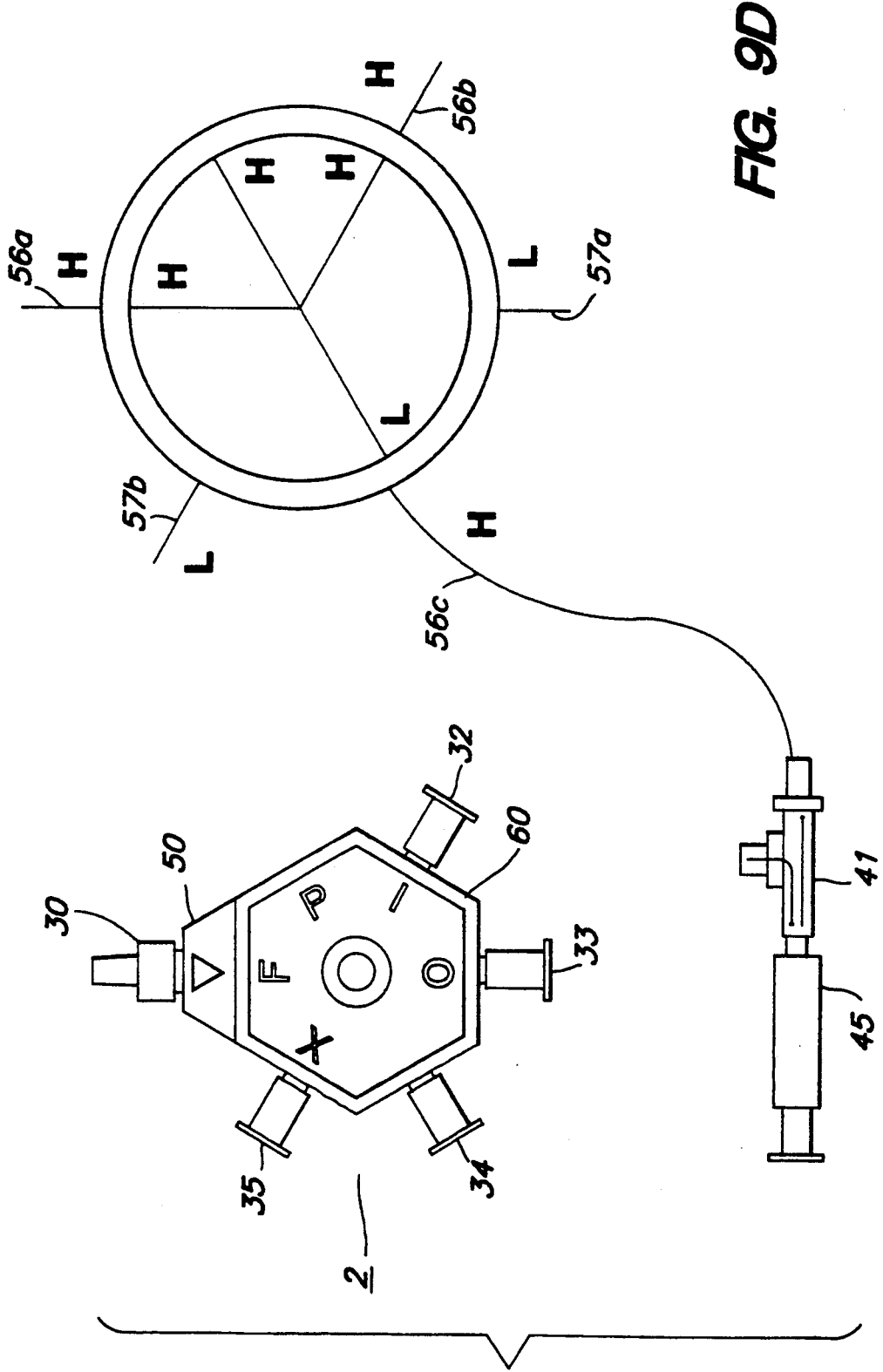

FIG. 9D shows the valve 2 in the F (flush) position. In this state, the 120° channel 11 of the valve stem 10 connects the catheter part 30 with the saline flush port 32, so the catheter 40 can be flushed with saline solution. Alternatively, fluid can be aspirated from the catheter 40 through the saline flush port 32. At the same time, the contrast dye can be loaded into the syringe 45.

Figure 9E:
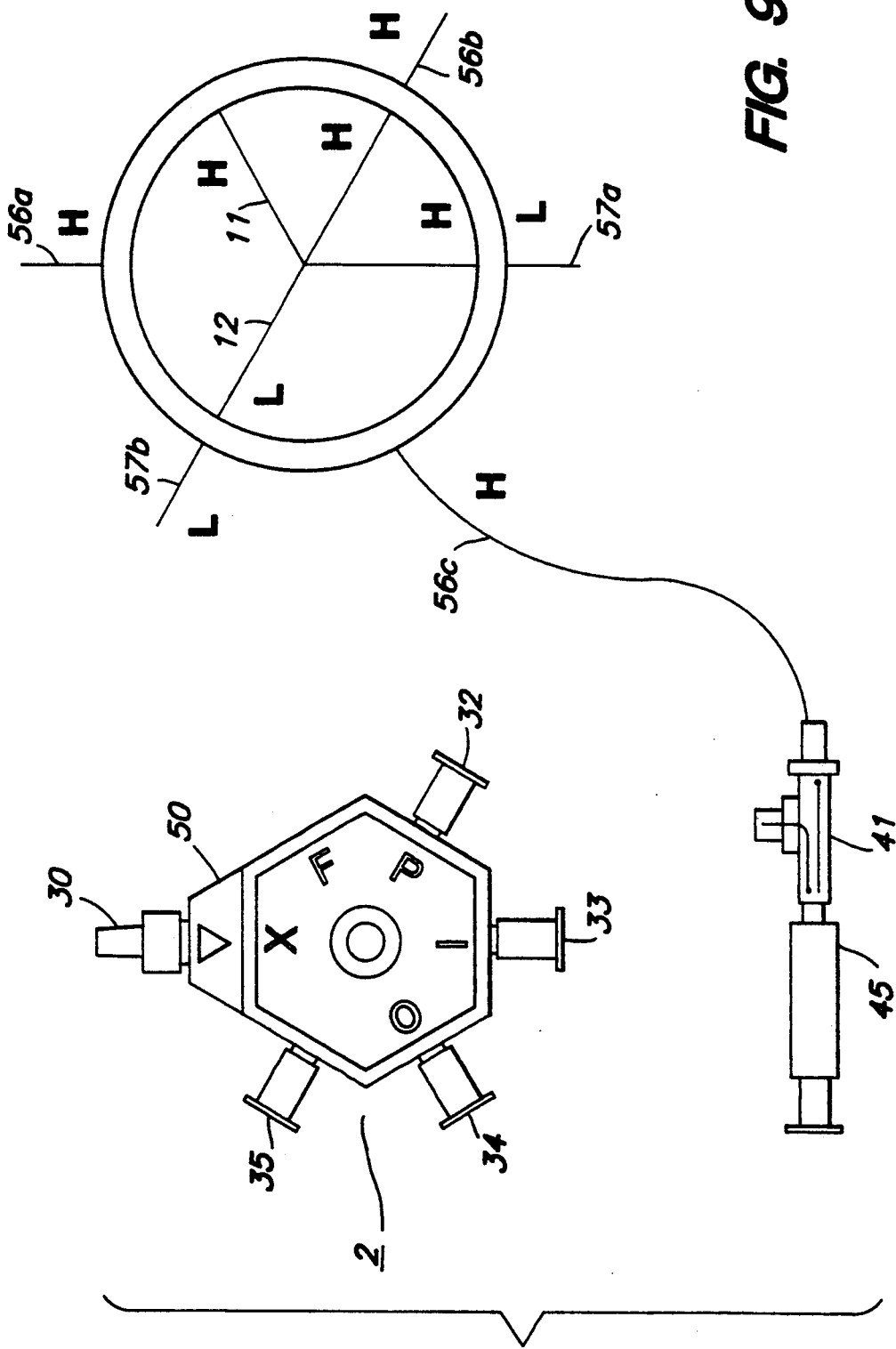

In FIG. 9E, the valve 2 is shown in the X (exhaust) position, in which the straight channel 12 of the valve stem 10 connects the saline flush port 32 with the flush exhaust port 35. In this position, fluid can be discharged from the valve stem 10 into the flush exhaust port 35. This position is typically used if a new drug has been connected to the saline flush port 32 and it is necessary to exhaust any small air bubbles which may be generated during the connecting operation. At the same time, the contrast dye can be loaded into the syringe 45.

The functions of the various positions are summarized in the following table.

TABLE 2

| Handle Position | Active Channel in Valve Stem | Clinical Function |
|---|---|---|
| O (off) | none | Change fittings. |
| I (inject) | 120° | Inject contrast dye into catheter. |
| P (pressure) | straight | Monitor fluid pressure in catheter. |
| F (flush) | 120° | Flush saline through catheter; aspirate catheter. |
| X (exhaust) | straight | Exhaust fluid or air bubble from flush port. |

This embodiment has the advantage that it is extremely easy for a user to determine whether the channels 11 or 12 in the valve stem 10 are precisely aligned with the channels (56a, 56b, 57a, and 57b) in the valve body 50 by making sure that one of the sides of the handle 60 is flush with one of the three lower sides of the valve body 50. Furthermore, the O (off) position enables a user to connect or disconnect equipment from the valve 2 without any discharge of fluid from the inside of the valve 2.

Figure 10:
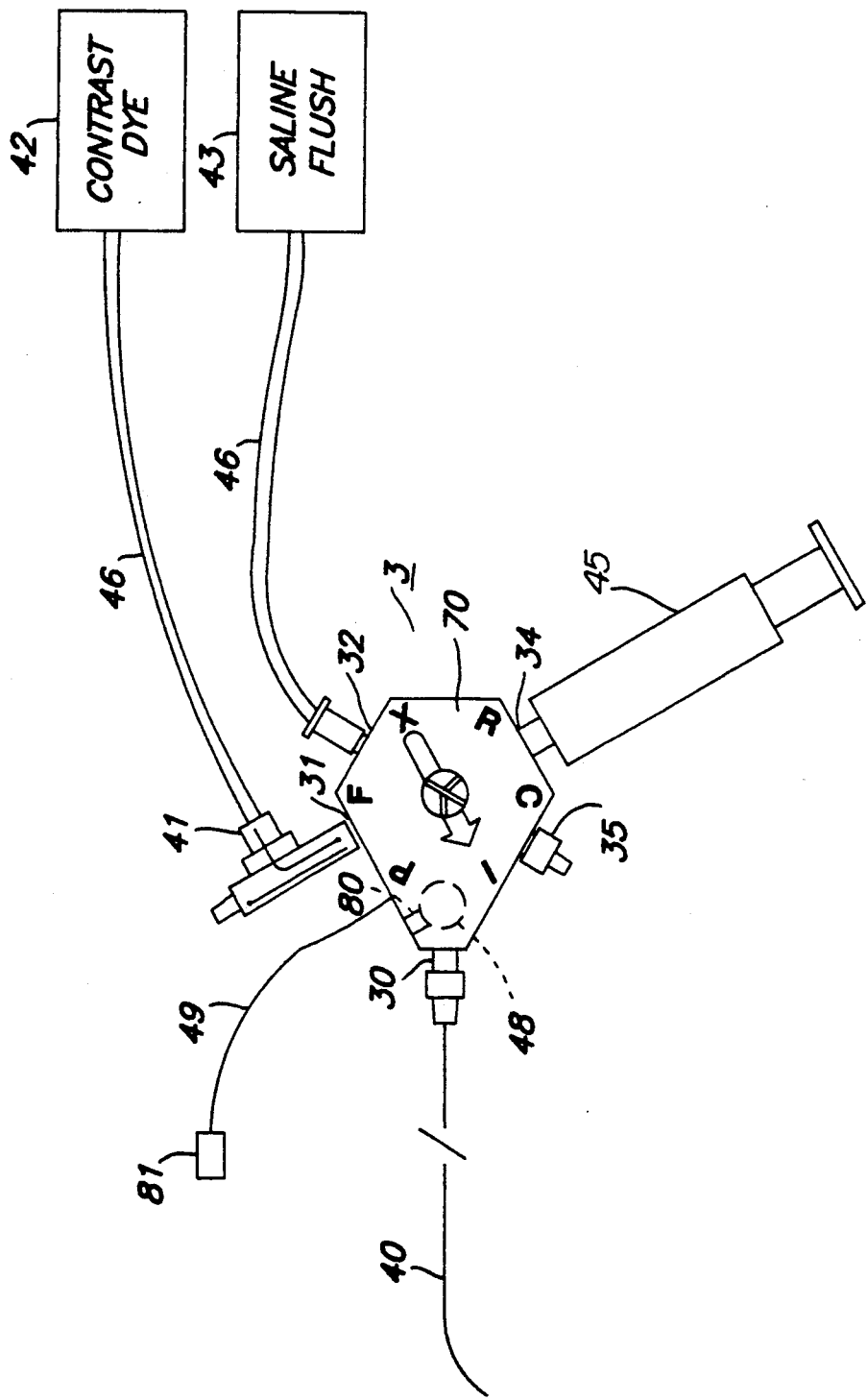
FIG. 10 is a schematic plan view of an arrangement for administration of a fluid employing a third embodiment of the present invention.

In some embodiments of the invention, a pressure transducer 44 is disposed on the outside of the valve body and is connected to the valve body by tubing 46c. However, the tubing 46c may dampen the heart pressure waves transmitted through the catheter 40, therefore possibly reducing the accuracy of pressure measurement. FIG. 10 illustrates another embodiment of the invention wherein a valve 3 houses inside the valve body 70 a pressure transducer 48 which directly communicates with a channel leading to the catheter port 30. This provides for direct conversion of the heart pressure wave into an electrical output signal within the fluid management valve itself, and, by eliminating the wave dampening pressure tubing required between the valve and stand-alone transducer, produces a higher fidelity pressure signal.

Figure 11A:
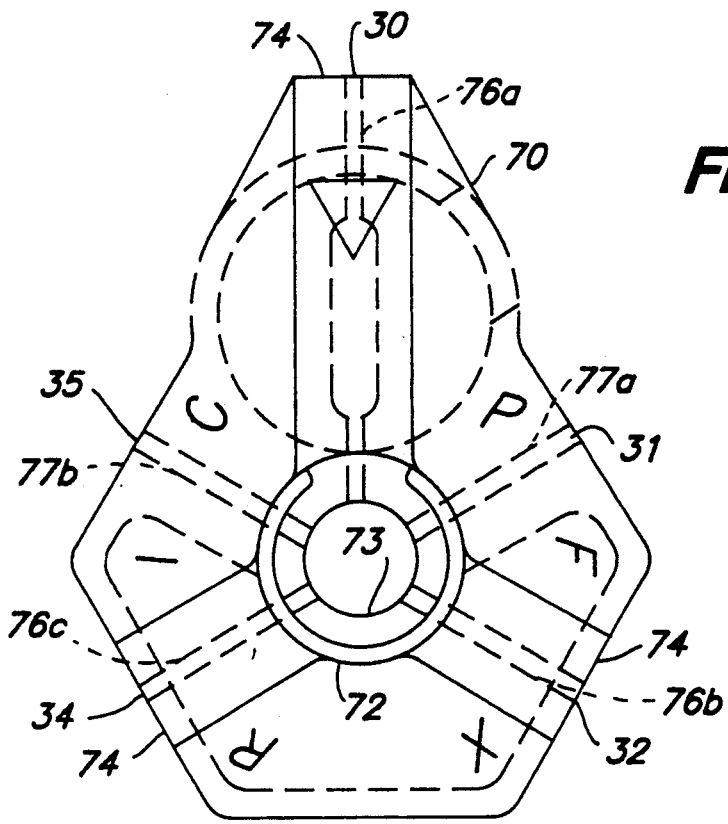
FIGS. 11A and 11B are respectively a top view and a bottom view of the valve body of the embodiment of FIG. 10.
Figure 11B:
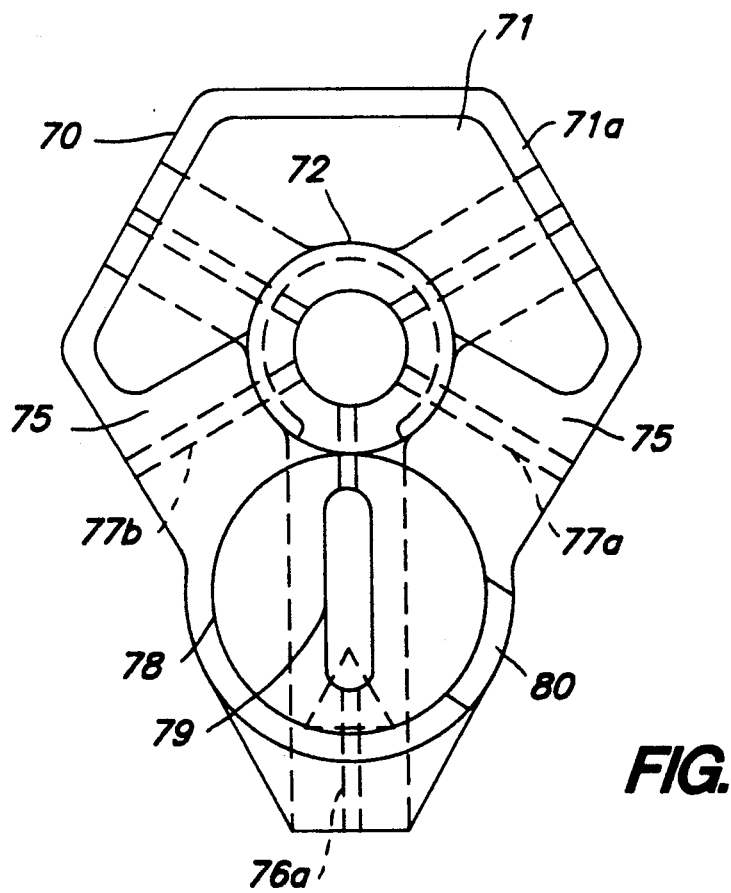

FIGS. 11A and 11B illustrate an embodiment of the invention having a valve body 70 which includes a base 71 having a cylindrical boss 72 containing a cylindrical bore 73. Three upper ribs 74 which extend radially outward from the boss 72 are formed on the upper surface of the base 71. The three upper ribs 74 are preferably separated from one another by 120°. First through third upper channels 76a–76c are formed in the upper ribs 74. Each upper channel has an inner end which opens onto the inside of the bore 73 and an outer end which opens onto the periphery of the base 71. Two lower structures 75, preferably spaced from one another by 120° and preferably spaced from the upper ribs 74 by 60°, are formed on the lower surface of the base 71. The lower structure 75 contain first and second lower channels 77a and 77b extending between the outer periphery of the valve body 70 and the inside of the bore 73. A compartment 78 for housing a pressure transducer is formed on the lower surface of the base 71 between the two lower structures 75. Electrical leads (not shown) extend from the transducer at opening 80. The inside of the compartment 78 communicates with the first upper channel 76a leading to the catheter port 30 via a passage 79. As shown in FIG. 10, an opening 80 for a transducer cable 49 may extend between the inside of the compartment 78 and the outer surface of the valve body 70. The cable 49 may be connected to an electronic recording device 81 for recording the output of the transducer. A catheter 40, a contrast dye reservoir 42, a saline flush reservoir 43, and a syringe 45 may be connected to the valve 3 in the same manner as in the embodiment of FIG. 1. The flush exhaust port 35 may be connected to a reservoir for waste fluids.

The upper surface of the valve body 70 may be marked with the same symbols as in the embodiment of FIG. 1. The handle 15 and the valve stem 10 may be identical or similar to those employed in the embodiment of FIG. 1. Alternatively, a hexagonal handle 60, similar to the one illustrated in FIG. 6 can be employed.

Various types of pressure transducers can be employed in this embodiment. One suitable type of transducer is a strain gauge pressure sensor chip housed in a circular thermoplastic package measuring 0.6 inches in diameter and 0.2 inches in thickness. The chip and electrical connections can be separated from the fluid pathway with a gel die coat. In a preferred embodiment a Motorola MPX2040D silicon pressure sensor provides good results. Whatever type of pressure transducer is employed, precautions should be taken to ensure that it is not damaged by the pressure in the first upper channel 76a leading to the catheter port 30, which may reach 1000 to 1500 psig when a contrast dye is being injected into a ventricle or a large peripheral artery. If the pressure transducer does not have a sufficiently high pressure capability, a passive over-pressure protector may be installed in the area between the compartment 78 for the pressure transducer and the first upper channel 76a. The over-pressure protector may be in the form of a spring-loaded valve which automatically closes to seal off the compartment when the pressure in the first upper channel 76a reaches a prescribed level. When the pressure falls below the prescribed level, the valve would automatically reopen and the pressure transducer could continue to monitor the pressure in the catheter 40.

The operation of this embodiment is substantially the same as that of the embodiment of FIG. 1.

What is claimed is:

1. A fluid control valve comprising:
   a valve body having a cylindrical bore and at least three input channels and an output channel for fluid flow formed therein, each of the channels having an inner end which opens onto the bore and an outer end which communicates with an outer surface of the valve body, the inner ends of at least two of the input channels respectively lying in first and second spaced, parallel planes; and
   a valve stem which is rotatably mounted in the bore of the valve body, the valve stem having a first channel and a second channel which is independent of the first channel formed therein, each channel in the valve stem being configured to connect the output channel with any one of but only one input channel in the valve body at a predetermined rotative position and at least one of the channels in the valve stem having a first end lying in the first plane and a second end lying in the second plane.

2. The fluid control valve of claim 1 wherein the channels in the valve body comprise:
   three input channels having inner ends lying in a first plane, the inner ends equidistant from one another as measured from an axis passing through the bore of the valve body; and
   two input channels having inner ends lying in a second plane and spaced about 120° apart as measured from the axis, at least one of the inner ends in the second plane being spaced from at least one of the inner ends in the first plane by 60° as measured from the axis.

3. A valve as claimed in claim 2 further comprising a sixth channel wherein the channels in the valve body include three channels having inner ends lying in the second plane, the three inner ends being equidistantly spaced from one another as measured from the axis.

4. A valve as claimed in claim 1 further comprising a compartment which communicates with one of the channels in the valve body and a pressure transducer housed in the compartment.

5. The fluid control valve of claim 1 wherein a channel in the valve stem has first and second ends in the first plane.

6. A fluid control valve comprising:
   a valve body having a cylindrical bore and at least three input channels and an output channel for fluid flow formed therein, each of the channels having an inner end which opens onto the bore and an outer end which communicates with an outer surface of the valve body, the inner ends of at least two of the input channels respectively lying in first and second spaced, parallel planes;
   a valve stem which is rotatably mounted in the bore of the valve body, the valve stem having a first channel and a second channel which is independent of the first channel formed therein, each channel in the valve stem being configured to connect the output channel with any one of but only one input channel in the valve body at a predetermined rotative position and at least one of the channels in the valve stem having a first end lying in the first plane and a second end lying in the second plane;
   a handle secured to the valve stem; and
   a setting indicator located on the valve body for indicating the setting of the valve corresponding to a rotational angle of the handle relative to the valve body.

7. A fluid control valve comprising:
   a valve body having a cylindrical bore and at least three input channels and one input channel for fluid flow formed therein, each of the channels having an inner end which opens onto the bore and an outer end which communicates with an outer surface of the valve body, the inner ends of at least two of the input channels respectively lying in first and second spaced, parallel planes;
   a valve stem which is rotatably mounted in the bore of the valve body, the valve stem having a first channel and a second channel which is independent of the first channel formed therein, each channel in the valve stem being configured to connect the output channel with any one of but only one input channel in the valve body at a predetermined rotative position and at least one of the channels in the valve stem having a first end lying in the first plane and a second end lying in the second plane; and
   a flow path indicator for indicating the flow path of a fluid through the valve body based on the relative rotational position of the valve stem to the valve body.

8. A fluid control valve comprising:
   a valve body having a cylindrical bore and at least three channels for fluid flow formed therein, each of the channels having an inner end which opens onto the bore and an outer end which communicates with an outer surface of the valve body, the inner ends of at least two of the channels respectively lying in first and second spaced, parallel planes;
   a valve stem which is rotatably mounted in the bore of the valve body, the valve stem having a first channel and a second channel which is independent of the first channel formed therein, each channel in the valve stem being configured to connect at least two of the channels in the valve body at a predetermined rotative position and at least one of the channels in the valve stem having a first end lying in the first plane and a second end lying in the second plane; and
   a handle which is secured to the valve stem and which has the shape of a regular polygon having a plurality of sides of equal lengths, wherein the valve body has at least one side which is equal in length to the sides of the valve handle and wherein one of the channels in the valve stem is aligned with one of the channels in the valve body whenever one of the sides of the handle is aligned with the side of the same length of the valve body.

9. A fluid control valve comprising:
   a valve body having a cylindrical bore and at least three channels for fluid flow formed therein, each of the channels having an inner end which opens onto the bore and an outer end which communicates with an outer surface of the valve body, the inner ends of at least two of the channels respectively lying in first and second spaced, parallel planes;
   a valve stem which is rotatably mounted in the bore of the valve body, the valve stem having a first channel and a second channel which is independent of the first channel formed therein, each channel in the valve stem being configured to connect at least two of the channels in the valve body at a predetermined rotative position and at least one of the channels in the valve stem having a first end lying in the first plane and a second end lying in the second plane;

a compartment which communicates with one of the channels in the valve body and a pressure transducer housed in the compartment; and a pressure-sensitive valve disposed between the compartment and the channel for preventing fluid communication between the compartment and the channel when the pressure in the channel exceeds a prescribed level.

10. An apparatus for administering fluids via a catheter comprising:

a valve body having a cylindrical bore and first through fifth channels formed therein, each of the channels having an inner end which opens onto the inside of the bore and an outer end which opens onto the outside of the valve body, the inner ends of the first, third and fifth channels lying in a first plane and being spaced from one another by 120°, the inner end of the second and fourth channels lying in a second plane which is parallel to the first plane and being space from one another by 120° and from the inner ends of the other channels by 60°;

a valve stem which is rotatably disposed in the bore and has a first channel having two ends lying in the first plane and spaced from one another by 120° and a second channel having two ends spaced from one another by 180°, one of which lies in the first plane and the other of which lies in the second plane;

a syringe which communicates with the outer end of the first channel;

a catheter which communicates with the outer end of the third channel;

a dual check valve which is connected to the outer end of the fourth channel and has an inflow and an outflow port;

a reservoir for a contrast dye which is connected to the inflow port of the dual check valve; and a reservoir for a saline solution which communicates with the outer end of the fifth channel.

11. An apparatus as claimed in claim 10 further comprising:

a sixth channel formed in the valve body and having an inner end which lies in the second plane and opens onto the bore of the valve body and an outer end which opens onto the outside of the valve body; and a pressure transducer which communicates with the outer end of the sixth channel.

12. An apparatus as claimed in claim 10 further comprising:

a transducer compartment formed in the valve body and communicating with the third channel;

a pressure transducer housed in the transducer compartment.

13. An apparatus as claimed in claim 12 further comprising:

a passage connecting the transducer compartment with the third channel; and a pressure-sensitive valve disposed in the passage for closing the passage when the pressure in the passage exceeds a prescribed level.

14. A fluid control valve comprising:

a valve body having a cylindrical bore and at least three output channels and an input channel for fluid flow formed therein, each of the channels having an inner end which opens onto the bore and an outer end which communicates with an outer surface of the valve body, the inner ends of at least two of the output channels respectively lying in first and second spaced, parallel planes; and a valve stem which is rotatably mounted in the bore of the valve body, the valve stem having a first channel and a second channel which is independent of the first channel formed therein, each channel in the valve stem being configured to connect the input channel with only one output channel in the valve body at a predetermined rotative position and at least one of the channels in the valve stem having a first end lying in the first plane and a second end lying in the second plane.

* * * * *